United States Patent [19]

O'Young et al.

[11] Patent Number: 5,198,597

[45] Date of Patent: Mar. 30, 1993

[54] BIMETALLIC CATALYSTS FOR DEHYDROISOMERIZATION OF N-BUTANE TO ISOBUTENE

[75] Inventors: Chi-Lin O'Young, Poughkeepsie; James E. Browne, Beacon; John F. Matteo, Wappingers Falls; Robert A. Sawicki, Stormville; John Hazen, Cragsmoor, all of N.Y.

[73] Assignee: Texaco Inc., White Plains, N.Y.

[21] Appl. No.: 738,017

[22] Filed: Jul. 30, 1991

[51] Int. Cl.$^5$ .......................... C07C 5/327; C07C 5/22
[52] U.S. Cl. .................................... 585/654; 585/671; 585/739; 585/740
[58] Field of Search ............... 585/660, 661, 671, 654, 585/739, 740

[56] References Cited

U.S. PATENT DOCUMENTS 4,392,003  7/1983  Kolombos et al. ................. 585/671
4,433,190  2/1984  Sikkenga et al. .................... 585/660

Primary Examiner—Anthony McFarlane
Assistant Examiner—Nhat D. Phan
Attorney, Agent, or Firm—James J. O'Loughlin; Vincent A. Mallare

[57] ABSTRACT

Normal olefins such as n-butenes and normal alkanes such as n-butane can be coverted to branched olefin species such as isobutylene by skeletal dehydroisomerization over catalysts preferably containing metals selected from Groups IB, IIB, IIIB, IVB, VB, VIB, VIIB, VIII and the rear earth elements which are deposited upon borosilicate zeolites having pore sizes of at least about 5 Angstroms and containing boron in the framework structure thereof. The borosilicates have sufficient acidity to catalyze the skeletal isomerization of both normal alkanes and normal olefins. The catalysts can be used to produce isoolefins for reaction with alcohols in integrated processes to produce alkyl tertiary alkyl ethers such as MTBE.

1 Claim, 3 Drawing Sheets

INTEGRATED ISOMERIZATION/MTBE PRODUCTION

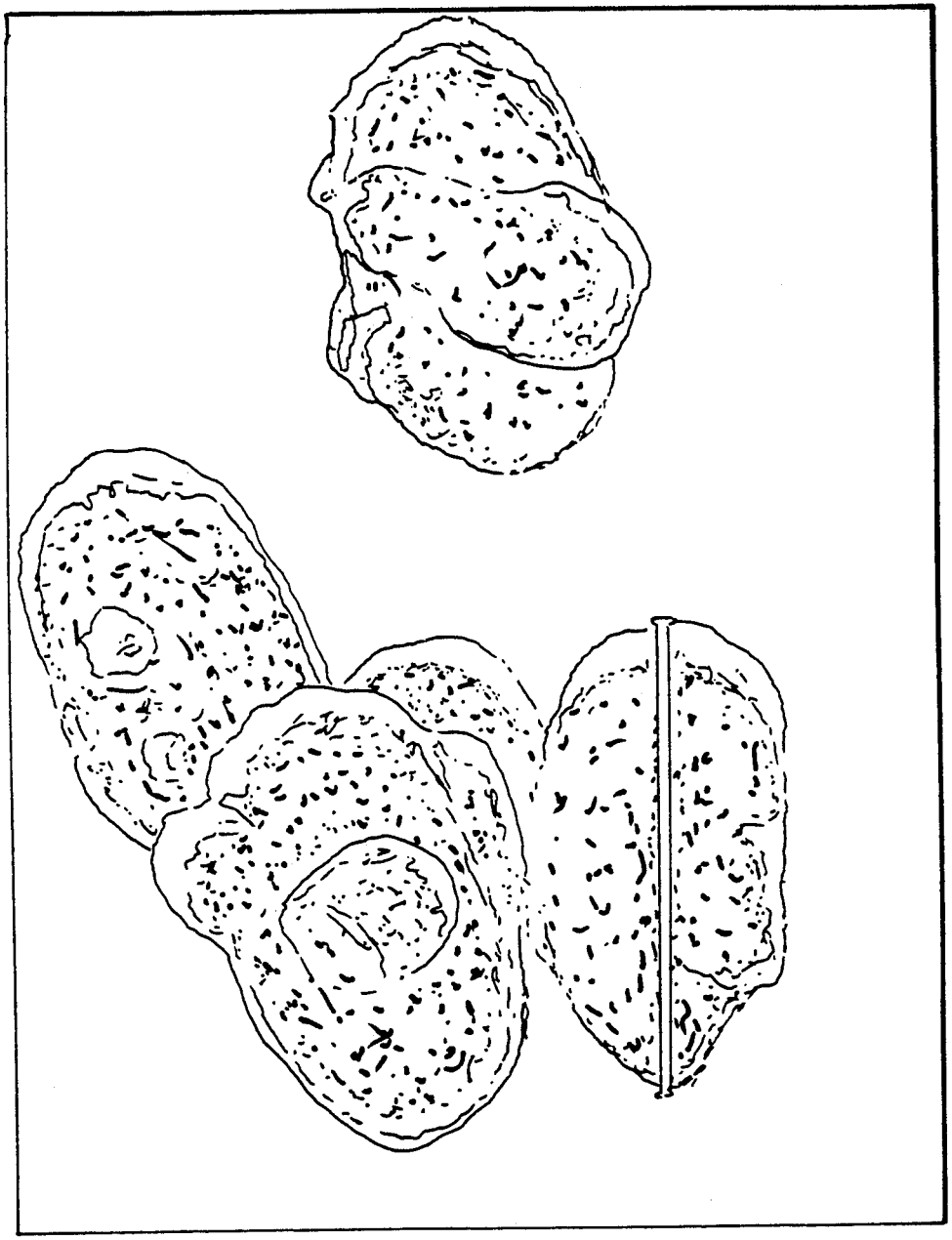
FIG. 2 SEM OF (B)-ZSM-11

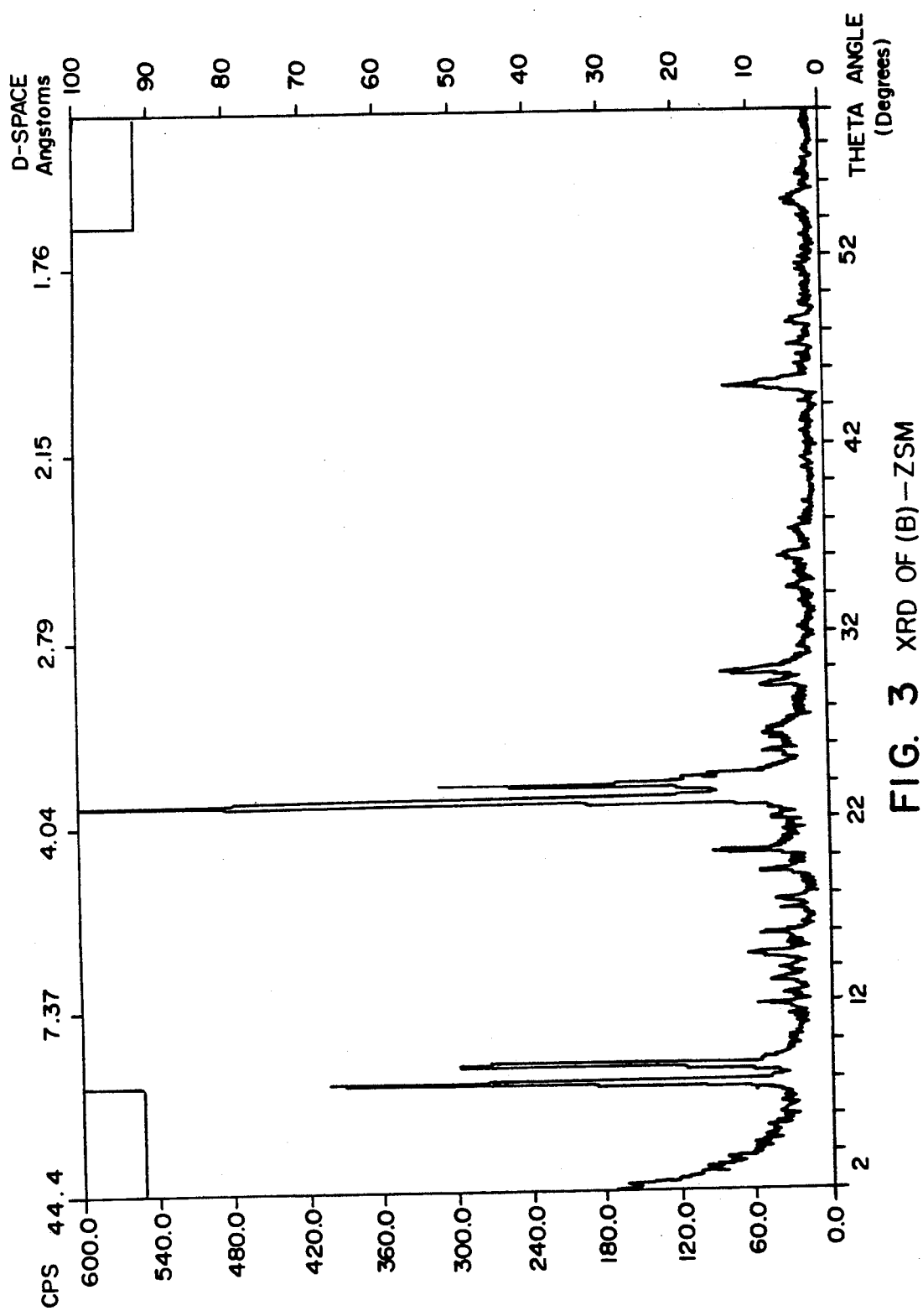
FIG. 3 XRD OF (B)—ZSM

BIMETALLIC CATALYSTS FOR DEHYDROISOMERIZATION OF N-BUTANE TO ISOBUTENE

BACKGROUND OF THE INVENTION

The present invention relates to a process for the preparation of isoalkenes and other useful hydrocarbons by catalytic conversion of n-alkanes, bimetallic catalysts which are suitable for this conversion, and a process for the preparation of such catalysts.

This invention further relates to dehydroisomerization of alkanes.

n-butane is presently a major component of gasoline. It is relatively cheap and plentiful and offers a high octane blending value. However, its Reid vapor pressure (RVP) is very high. Recently, the Environmental Protection Agency (EPA) issued a new proposal to reduce the permitted gasoline RVP from 11.5 psi to 10.5 psi in 1989 and further to 9.0 psi in 1992 as one way to cut hydrocarbon emissions and to lower ozone levels in the atmosphere. These new regulations will prevent refineries from using the highly volatile n-butane as a blending stock during the hot summer season. It is estimated that every one psi reduction in permitted gasoline vapor pressure will lead to a seasonal surplus of 80,000–130,000 bbl/day of n-butane. Therefore, how to utilize the surplus n-butane and to convert it to more valuable products are major concerns for most refineries and n-butane suppliers at this time.

MTBE (methyl tertiary butyl ether) is an effective octane booster. It is made from isobutylene and methanol. The present sources of isobutylene for MTBE production are mainly from by products of steam and catalytic crackers. However, these supplies are limited. Other possible sources are by isomerization of n-butenes taken from steam or catalytic crackers and by dehydrogenation of isobutane taken from field butanes or produced by isomerization of n-butane.

Olefin isomerization processes can be directed towards either skeletal isomerization or double bond isomerization. Skeletal isomerization is concerned with reorientation of the molecular structure in respect to the formation or elimination of side chains. Double bond isomerization is concerned with relocation of the double bond between carbon atoms while maintaining the backbone of the carbon structure. Most isomerization processes give rise only to double bond isomerization.

The minimum Brönsted Acid strengths (and equivalents in $H_2SO_4$) required for various acid-catalyzed conversions of hydrocarbons are indicated in the table below.

| Minimum Brönsted Acid Strength Required For The Acid-Catalyzed Conversions of Hydrocarbons | |
|---|---|
| $H_R$ Required | Reaction Type |
| < + 0.8<br>1.2 wt % $H_2SO_4$ | Cis-trans Isomerization of Olefins |
| < − 6.6<br>48 wt % $H_2SO_4$ | Double-bond Migration |
| < − 11.6<br>68 wt % $H_2SO_4$ | Skeletal Isomerization |
| < − 16.0<br>88 wt % $H_2SO_4$ | Cracking of Alkanes |

It is frequently necessary to convert olefins into other olefins having a different skeletal arrangement. For example, normal butenes are converted into isobutene for polymerization, alkylation, disproportionation, etc. Similarly, normal amylenes must be converted to isoamylenes prior to dehydrogenation to isoprene.

While a number of catalytic materials possess some activity for such a conversion, not all possess sufficient selectivity to be economical. Because the feeds are generally the relatively reactive olefins, many catalysts cause undesirable side reactions such as polymerization or cracking. Consequently, there is a continuing interest in the development of new skeletal isomerization catalysts and processes for isomerizing alkanes as well as alkenes to improve efficiencies and to give optimum results for various industrial requirements. A comprehensive review is provided by V. R. Choudhary in "Catalytic Isomerization of n-butene to Isobutene," *Chem. Ind.* Dev, pp. 32–41 (1974).

It is generally known that n-paraffins with, for example, 4 to 7 carbon atoms can be converted to the corresponding isomeric paraffins by using suitable acid catalysts in the temperature of from 100° to 250° C. Examples of this process are the numerous isomerization processes used in the petrochemical and mineral oil industries for increasing the octane number of light, paraffinic mineral oil fractions. Furthermore, it is known that, in contrast to this, olefins of the same number of carbon atoms cannot be converted to the corresponding isoolefins except under difficult conditions, for example at very high temperatures and with poor yield. The attempts hitherto described in the literature for the direct isomerization of the skeleton of e.g. n-butene to give isobutene or e.g. of n-pentene to give isopentenes over catalysts arranged in a fixed bed are characterized by only initially high yields and selectivities, which diminish and deteriorate considerably after a short period of operation, often after only a few hours. The deterioration in the yields and selectivities is generally attributed to the loss of actively effective catalyst surface or to the loss of active centers. In addition to this, high coking rates, formation of oligomers and cracking reactions are observed.

As is known, butylenes or butenes exist in four isomers: butene-1, cis-butene-2, its stereo-isomer transbutene-2, and isobutene. Conversions between the butenes-2 are known as geometric isomerization, whereas those between butene-1 and the butenes-2 are known variously as position isomerization, double-bond migration, or hydrogen-shift isomerization. These three isomers are not branched and are known collectively as normal or n-butenes. Conversion of the n-butenes to isobutene, which is a branched isomer, is widely known as skeletal isomerization. The same general terminology is used when discussing skeletal isomerization of other n-alkanes and n-alkenes.

Isobutene has become more and more important recently as one of the main raw materials used in the production of methyl tert-butyl ether (MTBE), an environmentally-approved octane booster to which more and more refiners are turning as metallic additives are phased out of gasoline production. However, processes for the skeletal isomerization of olefins e.g., to produce isobutene, are relatively non-selective, inefficient, and short-lived because of the unsaturated nature of these compounds. On the other hand, positional and skeletal isomerization of paraffins and alkyl aromatics are fairly well established processes, in general utilizing catalysts typically comprising metallic components and acidic components, under substantial hydrogen pressure. Since paraffins and aromatics are stable compounds, these processes are quite successful. The heavier the compounds, in fact, the less severe the operating requirements. Olefins, however, are relatively unstable compounds. Under hydrogen pressure, they are readily saturated to the paraffinic state.

Furthermore, in the presence of acidity, olefins can polymerize, crack and/or transfer hydrogen. Extensive polymerization would result in poor yields, and short operating cycles. Similarly, cracking would reduce yield. Hydrogen transfer would result in saturated and highly unsaturated compounds, the latter being the common precursors for gum and coke. Any theoretical one step process for producing skeletal isomers of, for example, n-butenes, would have to be concerned with the unwanted production of butanes and the reverse problem of production of butadienes. In addition to these problems, it is well known that skeletal isomerization becomes more difficult as hydrocarbons get lighter.

Skeletal isomerization of olefins is known to be accomplished by contacting unbranched or lightly branched olefins with acidic catalysts at elevated temperatures. The process is generally applicable to the isomerization of olefins having from 4 to about 20 carbon atoms and is especially applicable to olefins having from 4 to about 10 carbon atoms per molecule. The process may be used to form isobutene from normal butenes, methyl pentenes and dimethyl butenes from normal hexenes, and so forth.

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudhary, V. R., "Fluorine Promoted Catalysts: Activity and Surface Properties", Ind. *Eng. Chem., Prod. Res. Dev.*, 16(1), pp. 12-22 (1977) and U.S. Pat. No. 4,400,574. Numerous catalysts employ a metal or metal oxide in conjunction with a halide-treated metal oxide. For example, U.S. Pat. No. 4,410,753 discloses isomerization catalysts comprising $Bi_2O_3$ on fluorided alumina and U.S. Pat. No. 4,433,191 discloses skeletal isomerization catalysts comprising a Group VIII metal on halided alumina. Many of the catalysts including halide-treated components require periodic addition of halide materials to maintain catalyst activity; for example, see U.S. Pat. Nos. 3,558,734 and 3,730,958. An average yield for isobutene of 25 weight percent (within an observed range of 17 to 33 percent) is typically reported when using halided catalysts, based upon a review of various patents cited in this disclosure.

Various techniques have been employed to improve the effectiveness of materials such as alumina and silica as structural isomerization catalysts. For example, U.S. Pat. No. 3,558,733 discloses methods for activating alumina catalysts with steam, U.S. Pat. No. 4,405,500 discloses catalysts prepared by controlled deposition of silica on alumina and U.S. Pat. No. 4,587,375 discloses a steam-activated silicalite catalyst. In addition, various metal oxides have been used to improve the effectiveness of catalysts based upon alumina, silica or the like.

Zeolitic materials, especially in their hydrogen forms, are known to behave as strong acids. Due to their narrow yet regular pore size they are quite effective in catalyzing olefin polymerization. Unfortunately the pores are soon plugged due to deposition of polymeric materials and frequent catalyst regeneration is necessary to maintain activity.

Therefore, among the objects of this invention are improved processes for the dehydroisomerization of n-alkanes and olefins, especially for the dehydroisomerization of n-butanes to form isobutene. A more specific object is an easily prepared, stable, active multifunctional isomerization catalyst and processes for the skeletal isomerization of hydrocarbon species including n-alkanes and olefins. Other objects and advantages of the invention will be apparent from the following description, including the drawing and the appended claims.

DISCLOSURE STATEMENT

Amoco has patents disclosing that n-butane can be converted to isobutylene in one step, i.e. by dehydrogenation of n-butane to n-butenes and then by isomerization of n-butenes to isobutylene. For example, see U.S. Pat. Nos. 4,435,311 and 4,433,190 and other co-assigned patents referred to therein. The catalysts employed contain an AMS-1B borosilicate (also called [B]-ZSM-5 or Boralite C) and a noble metal such as platinum. This process is economically quite attractive because two catalytic reactions, dehydrogenation and isomerization, are carried out in one step by a bifunctional catalyst. Such reactions could potentially solve the surplus n-butane problem and produce high-octane MTBE.

Natural and synthetic zeolites have been widely used as catalysts, catalyst supports and the like for processes of hydrocarbon conversion. Additional components such as metals, in the elemental, oxide or cation form are often included in such catalysts. For example, U.S. Pat. No. 3,849,340 discloses a "catalytic composite" comprising a mordenite having a silica/alumina ratio of at least 40:1 and a metal component selected from copper, silver and zirconium. U.S. Pat. No. 4,608,355 also discloses hydrocarbon conversion catalysts formed by compositing a clay matrixing material with a zeolite containing cations of Group IB metals such as silver. The presence of such cations is said to give the zeolite improved resistance to high sintering temperatures encountered in catalyst fabrication. The metal loaded zeolites can be mixed with a porous matrix and calcined prior to use. These catalysts are stated to be useful in processes such as catalytic cracking, the conversion of oxygenates to hydrocarbons, and the like.

U.S. Pat. No. 4,433,190, assigned to Standard Oil Co. (Indiana), discloses processes for the conversion of alkanes such as n-butane to dehydrogenated and isomerized products by contact with catalysts containing AMS-1B crystalline borosilicates containing ions or molecules of catalytically active elements such as noble metals. These borosilicates have topological structures similar to those of ZSM-5 zeolites. The products can include isobutylene, n-butene and isobutane.

U.S. Pat. No. 4,503,282, also assigned to Standard Oil Co. (Indiana), discloses processes for converting n-alkenes to isoalkenes using catalysts containing AMS-1B borosilicate as at least 50 weight percent of the catalyst composition. The borosilicate can be cation-exchanged with hydrogen or metals selected from Groups IB, IIA, IIB, IIIA, VIB and VIII as well as manganese, vanadium, chromium, uranium and rare earth elements. The borosilicate can also be impregnated with metals of Groups IB, IIA, IIB, IIIA, IVB, VB, VIB, VIIB and VIII and rare earth elements.

U.S. Pat. No. 4,435,311, also assigned to Standard Oil Co. (Indiana) discloses a process for regenerating catalysts containing AMS-1B borosilicates and noble metals by contacting them with water. The process can be carried out during the process of conversion of feedstocks such as alkanes and alkenes to isomerized products such as isoolefins. Similar conversion processes employing catalysts containing such borosilicates are disclosed in U.S. Pat. Nos. 4,777,310; 4,503,282; 4,499,325 and 4,499,326, all assigned to Standard Oil or Amoco Corp.

U.S. Pat. No. 4,656,016 discloses silicalites and similar silica-based molecular sieves which contain boron or other amphoteric elements in quantities sufficient to adjust the acidity of the sieves, plus catalytic metals such as copper, nickel, cobalt, tungsten, platinum and palladium. The reactions which can be catalyzed by such materials are listed in column 4, including hydrogenation/dehydrogenation of hydrocarbons and conversion of olefins into "high-octane fuel products." Columns 9 and 10 contain descriptions of silicalites containing boron in the framework structure, referred to as "Boralites A, B, C and D." These species are identified as having structures resembling those of zeolites NU-1, Beta, ZSM-5 and ZSM-11, respectively, by Taramasso et al in "Molecular Sieve Borosilicates", in Proceedings, 5th Intl. Conference on Zeolites, pp. 40–48, Naples, 1980 (L. V. Rees, ed.)—(Heyden, London, 1980).

SUMMARY OF THE INVENTION

In accordance with the present invention, a bimetallic multifunctional catalyst composition for the skeletal isomerization of normal alkanes and olefins comprises at least one borosilicate zeolite and optionally at least one dehydrogenation metal selected from the group consisting of Groups IB, IIB, IIIB, IVB, VB, VIB, VIIB and VIII, the rare earth metals, and combinations thereof. Preferred metals include the noble metals such as platinum, palladium, rhenium and rhodium. A binder of an inorganic oxide such as alumina, silica, silica-alumina, clays and combinations thereof can optionally be employed.

The borosilicate zeolites are prepared by a process comprising the steps of:
(a) preparing a basic reaction mixture of at least about pH 9 comprising in suitable proportions a silicon source, a boron source and an organic template;
(b) heating the reaction mixture in a closed vessel under conditions of temperature, autogenous pressure and time effective to produce a crystalline product containing boron oxides in the framework structure thereof;
(c) recovering the crystalline product; and
(d) calcining the crystalline product conditions effective to remove the organic template without substantial damage to the framework structure of the crystalline product.

To achieve the calcining effect which removes the organic template without damaging the crystal structure, the product is preferably subjected to at least one period of calcining in an inert atmosphere such as nitrogen, followed by at least one period of calcining in an atmosphere containing oxygen. The zeolites can be converted to the hydrogen form by cation-exchanging with ammonium ion to remove sodium, then calcining to remove ammonia. The exchange step can be eliminated if certain organic templates containing tetraalkyl ammonium ions are used, as calcining drives off ammonia and organic residues, with hydrogen ions remaining.

Such boron-substituted zeolites, optionally in combination with dehydrogenation metals as described below, can be employed in catalysts having activity for the structural isomerization or dehydroisomerizatin of normal alkanes such as butane, the dehydrogenation of isoalkanes such as isobutane and the structural isomerization of normal alkenes such as n-butenes. Such catalysts can be used to treat mixed feedstreams containing such species to products rich in isoolefins such as isobutene. Byproducts including such species can be recycled to the reactor for additional passes so as to maximize the conversion to the desired product(s). The isoolefins are desired reactants in the production of alkyl tertiary-alkyl ethers such as methyl tertiary-butyl ether, and processes for the production of such ethers can be integrated with the hydrocarbon conversion processes of the present invention.

Further in accordance with the present invention, processes for converting normal olefins and/or alkanes to branched chain olefins by skeletal isomerization comprise steps of contacting the olefins and/or alkanes (which can be at least about 20 weight percent of a mixed feedstock) under skeletal isomerization conditions with a multifunctional catalyst of the invention. The catalyst can include a boron-substituted zeolite containing sufficient boron to provide sufficient acidity in the zeolite to catalyze the skeletal isomerization of both normal alkanes and normal alkenes, preferably without substantial cracking. Optionally the catalyst includes at least one dehydrogenation metal selected from the group consisting of Groups IB, IIB, IIIB, IVB, VB, VIB, VIIB and VIII of the Periodic Table, plus rare earth metals. Preferably the metal is a noble metal selected from platinum, palladium, iridium, rhodium and ruthenium. Preferred embodiments include combinations of metals which are more effective in catalysts to be used at relatively high temperatures, for example noble metals in combination with rhenium. The boron-substituted zeolite should have a pore size of at least about 5 Angstroms, and preferably is characterized by a topological structure selected from the group consisting of ZSM-5, ZSM-11, NU-1, Beta, Omega (MAZ), FAU and mordenite (MOR) zeolites.

Operable conditions include temperatures in the range of about 300° to 650° C., preferably 500° to 600° C.; pressures ranging from about 2.0 to about 500 psi and weight hourly space velocities (wHSV) ranging from about 0.1 to about 100 weight of olefin/weight of catalyst per hour. The normal olefins and/or alkanes can have from 4 to about 12 carbon atoms, preferably about 4 to 6, and preferably include n-butene and/or n-butane.

In a preferred embodiment, the normal olefins are contained in a feedstock which also contains branched olefins, and the product of the skeletal isomerization step is reacted with an alkanol having from 1 to about 5 carbon atoms (such as methanol or ethanol) under catalytic conditions effective to produce at least one methyl tertiary-alkyl ether, such as methyl tertiary-butyl ether, or ethyl tertiary-butyl ether.

BRIEF DESCRIPTION OF THE DRAWINGS

FIG. 2 is a scanning electron micrograph illustrating the morphology of [B]-ZSM-11; and FIG. 3 is an X-ray diffraction spectrum of [B]-ZSM-11.

DETAILED DESCRIPTION OF THE INVENTION

Figure 1:
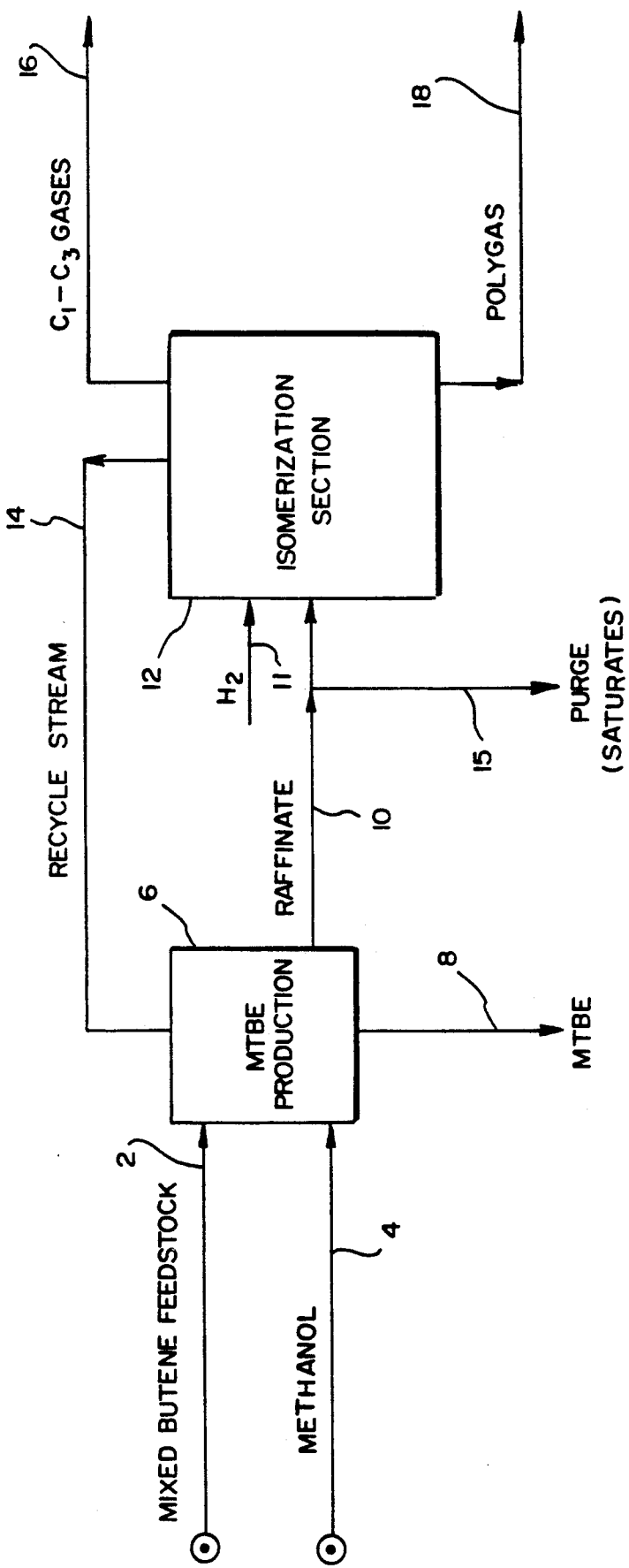
FIG. 1 is a schematic diagram for a process for the production of methyl tertiary-butyl ether (MTBE) which includes an isomerization section.

As discussed above, the skeletal isomerization catalysts of the present invention employ medium to large pore zeolites containing boron in the framework structures. For the purposes of this application, a medium pore zeolite is one with a channel of at least about size greater than 5Å, while the large pore channels are greater than 5.6 Å; the zeolite is preferably one with channels of 5.0 to 7.4 Å. Typical materials of this structural tYpe would include: mordenite, faujasite, X, Y, and L zeolites, mazzite, ZSM-4, ZSM-5, ZSM-11, zeolite omega, zeolite beta, ZSM-20, NU-1 and gmelinite.

The medium to large pore boron zeolites useful in the present invention are preferably selected from the groups of topologically-related zeolite structures listed below in tabular form and published in the *Atlas of Zeolite Structure Types* by Meier and Olson, published on behalf of the Structure Commission of the International Zeolite Association by Butterworths & Co. Ltd. (London, 1988), following rules set up by a Commission of Zeolite Nomenclature of the International Union of Pure and Applied Chemistry.

| FAU | MOR | MAZ | * |
|---|---|---|---|
| Faujasite | Mordenite | Mazzite | NU-1 |
| X (Linde) | Ptilolite | Omega | Beta |
| Y (Linde) | Zeolon | | |
| N-Y | | | |
| ZSM-20 | | | |

*No code assigned to this group.

Zeolite ZSM-20 is described in U.S. Pat. Nos. 3,972,983 and 4,021,331 and zeolite beta in U.S. Pat. No. 3,303,069 and Re. 28,341; zeolite L is disclosed in U.S. Pat. No. 3,216,789, zeolite omega is disclosed in U.S. Pat. No. 4,241,036, ZSM-4 is disclosed in U.S. Pat. No. 3,578,723, zeolite X is disclosed in U.S. Pat. No. 2,882,244 and zeolite Y is disclosed in U.S. Pat. No. 3,130,007; reference is made to these patents for details of these zeolites, their preparation and properties. Many suitable forms of these zeolites can be employed, including variations in silica/alumina ratio, silicon/boron ratio, cell size and the like.

Synthesis of Boron Substituted Zeolites

NU-1, Beta, ZSM-5, and ZSM-11 zeolites can be prepared by the same family of organic templates, tetraalkylammonium ions. The formation of each phase depends on the type of template used, on the reaction conditions, and on the gel composition. Table A below shows the types of zeolites and boron-zeolites which can be produced with tetraalkylammonium templates. ZSM-5 can be synthesized in the presence of TPA and TEA ions, while ZSM-11 can be synthesized in the presence of TBA ion. Both of these pentasil structures have frameworks containing two intersecting channel systems with 10-ring openings. For ZSM-11 the two channel systems are straight, but for ZSM-5 one channel is straight and the other one is zigzag or sinusoidal. See, e.g. Coudurier et al, *J. Catalysis*, Vol. 108, p. 1 (1987). [B]-ZSM-11 zeolites are presently preferred since they have outperformed [B]-ZSM-5, possibly at least in part because of the more open pore structure.

NU-1 and Beta zeolites can be synthesized in the presence of TMA and TEA ions, respectively. The structure of Beta has been solved recently. It has an interconnected tunnel system with 12-ring openings. The structure of NU-1 is not clear, but it seems to have a dual pore system with 10-rings and 8-rings based upon adsorption results reported by Dewing et al. in *Catal. Rev. Sci. Eng.*, Vol. 27, pp. 461 (1985).

Boron substituted ZSM-5 and ZSM-11 zeolites have been synthesized as described below, and catalysts prepared by adding platinum to either zeolites have shown promising results in converting n-butane to isobutylene. Boron substituted zeolites have much weaker acidity than aluminum zeolites, as reported by Chu et al. in *J. Catal.*, Vol. 93, pp. 451–458 (1985). Platinum loaded ZSM-5 catalysts reportedly show activity in converting n-butane to aromatic compounds, but no skeletal isomerization activity was observed because of the strong acidity, according to Inui et al., *J. Catal.*, Vol. 90, pp. 366 (1984). It is believed that the skeletal isomerization activity of platinum loaded [B]-ZSM-5 and [B]-ZSM-11 catalysts is due to the uniqueness of the low acidity of these zeolites. Thus, it should be possible to prepare the analogous [B]-NU-1 and [B]-Beta zeolites, and employ them in catalysts for the conversion of n-butane to isobutylene, since the pore systems of all these zeolites are believed to be large enough for the reactants, intermediates and products of such reactions.

TABLE A

Synthesis of Zeolites in the Presence of Tetraalkylammonium Ions.

| Template | (Al, Si) zeolite | (B, Si) zeolite |
|---|---|---|
| TMA | NU-1 | Boralite A/[B]-NU-1 |
| TEA | Beta and ZSM-5 | Boralite B/[B]-Beta and Boralite C/[B]-ZSM-5 |
| TPA | ZSM-5 | Boralite C/[B]-ZSM-5 |
| TBA | ZSM-11 | Boralite D/[B]-ZSM-11 |

TMA = tetramethylammonium ion, TEA = Tetraethylammonium ion, TPA = tetrapropylammonium ion, and TBA = Tetrabutylammonium ion.

Also preferred are zeolites with three dimensional pore structures such as the various forms of zeolite Y, since greater access to the reactants is offered. Zeolites characterized by the structure of zeolite Y are also preferred because they have been employed effectively in the examples herein.

When the zeolites are prepared in the presence of organic cations they are initially catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite but these cations to favor the formation of the desired crystal structures.

In commercial practice, the zeolite crystallites would be bound together within a matrix comprising alumina, silica-alumina, clay or admixtures thereof. Normally, the finished catalyst would contain at least 10 up to about 85 weight percent of such a binder or matrix. The alumina which is used for the matrix material for the catalyst system of the present invention can be any suitable grade of crystalline or amorphous alumina which is substantially inert. Since the boron zeolites employed have moderate acidity, acidic aluminas should be avoided. The alumina matrix should have a specific surface area of at least about 50 $m^2/g$, preferably in the range of from about 50 to about 500 $m^2/g$, and most preferably from about 100 to about 350 $m^2/g$.

Silica-alumina materials which can be used as binders can be prepared in the same manner as amorphous silica-alumina catalysts, e.g., by adding the zeolite component to a silica-alumina slurry, spray drying, washing the product and drying. Optionally, a clay diluent can be present in the silica-alumina slurry. Such matrixes can be prepared by admixing colloidal alumina (boehmite) and colloidal silica, allowing the matrix properties to vary over a wide range from catalytically inert to active. The activity, thermal stability, surface area and pore distribution of the matrix can be controlled by varying the amounts and particle size distributions of the respective colloids. Further guidance for the preparation of zeolite catalysts containing high porosity matrixes such as silica-alumina can be found in the section by Magee and Blazek on "Zeolite Cracking Catalysts" in ACS Monograph 171, *Zeolite Chemistry and Catalysts* (J. Rabo, Ed.; Am. Chem. Soc., Wash, D.C. 1976).

The zeolite can also be composited with a porous clay matrix material which has suitable binding properties and is resistant to the temperature and other conditions employed in the process. The composite is then calcined to confer the required physical strength. Naturally occurring clays can be composite with the zeolite and these clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie, McNamee-Georgia and Florida clays and others in which the main mineral constituent is halloysite, kaolinite, dickite, nacrite or anauxite. Other clays may also be found to be suitable for use in the present process.

The amount of clay or other matrix material relative to zeolite in the composite will determine, to a certain extent, the physical strength of the final catalyst, especially its attrition resistance and crushing strength. The mechanical properties of the catalyst can therefore be modified by appropriate choice of clay/zeolite ratio, with greater amounts of clay generally conferring better mechanical properties. On the other hand, larger amounts of clay mean that less of the zeolite with its desired, attendant properties will be available to participate in the eventual reaction. A balance will therefore be struck, in most cases, between activity and mechanical properties. Normally, the amount of zeolite will not exceed 50 percent by weight of the composite and in most cases it will not exceed 40 percent by weight and may be lower, e.g. 25 percent by weight or even 15 percent by weight.

The zeolite may conveniently be composited with the clay or other matrix materials by forming an aqueous slurry of the zeolite or zeolites containing the Group IB, VIII or other metal with the clay, spray drying the slurry to form microspheres and then calcining. The zeolite may be in the form of a gel. If the catalyst is to include more than one zeolite, the zeolite may form a cogel with themselves. If one of the zeolites in the zeolite combination is capable of being produced by treatment of a clay, the zeolite may be composited with the clay slurry and the slurry spray dried to form solid zeolite/clay microspheres which are then calcined to confer the desired strength. The clay in the composite may then be converted to the zeolite in the conventional way, e.g. by treatment with sodium hydroxide and heating, followed by ion-exchange, if desired. The mixing and homogenizing steps which may be used in the preparation of the zeolite-matrix mixtures are conventional and need not be described; the spray drying may also be carried out in the conventional manner.

For the catalysts of the present invention, suitable dehydrogenation metals (from Groups IB, IIB, IIIB, IVB, VB, VIB, VIIB and VIII of the Periodic Table of the elements, plus the rare earth elements) can be employed to make zeolites active for the skeletal isomerization of normal alkanes and/or olefins in the presence of hydrogen, especially when the cation-exchanged zeolites are pretreated with hydrogen to reduce the metal cations. The metals were selected according to several criteria in addition to the nature of the reactants and products desired, including the preference that they have a reduction potential value, $E°$, which is more positive than that of a standard hydrogen electrode (defined as $E° = 0.00$ volts). Among such metals, those which also require relatively low temperature pretreatment and activation include Ag, Cu, Pd, Pt, Re, Rh, Au and Ir, with cationic charges ranging from 1 to 4. Fe can also be used, requiring moderate pretreatment temperatures, say up to about 350° C. Ni, Co and Cd (which have $E°$ values between 0 and $-0.41$) can be used if higher pretreatment temperatures for reduction of the cations (up to about 550° C.) can be tolerated by the catalyst materials.

Since it is easier in practice to ion-exchange zeolites if the charge on the ion employed is low, cations of the metals above which have charges of 1 or 2 such as Ag and Cu are preferred on this basis. Among the noble metals of Group VIII, Pd, Pt, Ir, Re and Rh are preferred. The use of Re in combination with at least one of the other noble metals has been found to make the metals more resistant to sintering; thus, such combinations are preferred for high reaction temperatures. In other preferred embodiments, the metal can be selected from Ni, Co and Cd, provided higher pretreatment temperatures can be accepted. Alternatively, Pd or Pt can be used in conjunction with these metals to reduce the pre-treatment temperature requirement. See, e.g., Heinerman, et al., "Catalytic Activity of Nickel-Substituted Mica Montmorillonite," *J. Catalysis* Vol 80, pp. 145–53 (1983), which reports that Pd promotes the formation of zero-valent nickel in reduction by hydrogen.

The catalysts of the invention can be prepared by cation-exchanging the zeolite with the metal(s) by any suitable method. Ion-exchange operations on zeolites are quite common and can occur under ambient conditions. Higher temperatures and more concentrated solutions are used to ensure very high levels of exchange. Sometimes, three or more batchwise exchange treatments are required to obtain a reasonable exchange level. Silver exchange, for example, should not be a difficult operation, since it is easier in practice to ion-exchange zeolites with ions having low charges, but a copper or cadmium exchange may require the more strenuous procedures. If one is using the sodium or potassium form of the zeolite and does not carry out a full and complete exchange of all alkali with Ag, Cu or Au, one may use ammonium chloride as part of the exchange solution so that all of the alkali is exchanged with either the ammonium or an ion of Ag, Cu or Au.

The zeolite may be converted to the Group IB, VIII or other metal form by conventional ion-exchange techniques using, for example, an aqueous solution of the cation of the metal. When the metal cation being introduced into the zeolite is silver, for example, solutions of silver nitrate are useful and preferred. If the metal cation is copper, solutions of copper chloride, copper sulfate or copper nitrate may be used and if the metal cation is cadmium, solutions of cadmium chloride, sulfate or nitrate are suitable. Soluble gold halides such as the chlorides can be used. Suitable soluble compounds of the other metals discussed above can be readily selected. Methods of incorporating Group 1B metals into zeolites of the ZSM-5 type are described in U.S. Pat. No. 4,276,438 and reference is made to that patent for details of such methods and of suitable compounds of Group 1B metals for this purpose. Similar cation exchange methods may be employed with other metals and other zeolites such as the large pore zeolites. Preferably, at least about 40 percent of the zeolite's exchangeable sites are exchanged with the metal cations.

In addition to ion-exchange techniques, conventional impregnation techniques (e.g. aqueous solutions of silver nitrate or suitable solutions of other metal salts such as $(NH_3)_4PtCl_2$) could be used.

The dried impregnated catalyst precursor material is preferably treated with a reducing gas at a suitable temperature and for a time effective to at least partially convert the hydrogenation metal cations to their elemental forms. The temperature should be at least about 100° C., preferably ranging from about 100° C. to about 600° C., most preferably from about 300° C. to about 500° C. The highest temperatures may be required when metals which are difficult to reduce, such as Ni, are employed. The reducing treatment time can range from about 10 minutes to about 8 hours and preferably ranges from about 0.5 to about 6 hours. Since the objective is to convert the metal(s) employed to the(ir) elemental forms, treatment takes place in an atmosphere of a reducing gas such as hydrogen. The reducing gas can range from as little as about 2 volume percent in mixtures of inert industrial gases to substantially pure hydrogen or the like. It is presently preferred to use the reducing gas in a flowing current to remove impurities as the reduction proceeds. The gas pressure during treatment can range from subatmospheric to slightly elevated pressures, but is preferably about atmospheric pressure.

The impregnated catalysts can be dried in air under temperature and time conditions to reduce the overall moisture content to less about 5 weight percent. This drying step preferably is conducted at temperatures in the range of from about 80° to about 150° C., for suitable periods of time to attain the desired level of moisture content.

After the final reducing step, the dried catalyst material can optionally be treated so that the active metals are sulfided. This can involve several procedures. Suitable procedures for both reduction and sulfidation are disclosed in U.S. Pat. Nos. 4,433,190 and 4,435,311, which are incorporated herein by reference. One method is to load the material into the reactor, followed by contacting with sulfur- containing compounds. Such contacting can be by $H_2S$ mixed with $H_2$ in concentrations ranging from 0.5 to 20 weight percent and under conditions ranging from 250° to 500° C. and from 0 to 1000 psig, with a continuous flow at rates from 1 to 50 SCCM of gas per ml of catalyst and from 0.5 to 10 hrs. Alternatively, the catalyst can be contacted with a non-aqueous solution of a reactive sulfur- containing compound, such as thiols, sulfides and disulfides, including compounds such as propanethiol, butyl disulfide, or other suitable compounds. Solvents can include refinery hydrocarbon streams such as gas-oils, paraffinic liquids such as hexanes, or other suitable non-aqueous solvents. The solution, containing at least enough sulfur to stoichiometrically sulfide the catalyst, is contacted with the material to be sulfided by completing filling the catalyst bed or other vessel with the liquid under conditions ranging from 20° to 110° C. and from 0 to 1000 psig and from no flow to 10.0 LHSV for periods of time ranging from 0.5 to 10 hrs.

Alternatively, the liquid solution can be contacted with the material to be sulfided outside of the reactor, in any suitable equipment. The sulfided catalyst is then dried in an oxygen-free environment and placed into the reactor for use.

The dehydrogenation metals listed above are employed in proportions effective to produce a catalyst with skeletal isomerization activity for normal alkanes and/or olefins, generally at least about 0.05 weight percent of the finished catalyst, calculated for the elemental form of the metals. Preferably the metals are present in amounts ranging from about 0.05 to about 10 weight percent, and most preferably from about 0.1 to about 5 weight percent.

The dried impregnated catalyst precursor material is calcined at a suitable temperature and for a time effective to substantially convert the metals or compounds (e.g. $(NH_3)_4PtCl_2$) to their oxides. The temperature should be at least about 150° C., preferably ranging from about 200° C. to about 400° C., most preferably from about 280° C. to about 350° C. The calcining time can range from about 1 hour to about 8 hours and preferably ranges from about 2 to about 6 hours. Since the objective is to convert the metal(s) employed to the(ir) oxides, calcining takes place in an atmosphere of an oxygen-containing gas. The oxygen content can range from as little as about 2 volume percent in mixtures of inert industrial gases to substantially pure oxygen. It is presently preferred to use air in a flowing current to remove impurities as the calcining proceeds. The gas pressure during calcining can range from subatmospheric to slightly elevated pressures, but is preferably about atmospheric pressure.

Spent catalysts can be regenerated by heating in a similar oxygen-containing gas, such as air, at temperatures ranging from about 200° C. to about 700° C. This process is significantly simpler than that required for halided metal oxide catalysts, in which a separate step of replacing the halide component must be employed.

The skeletal isomerization processes of this invention are carried out by contacting the feed with the catalyst, using any suitable contacting techniques, at temperatures at which skeletal isomerization of the feed alkanes and/or olefins occurs. The feed is preferably maintained in the vapor phase during contacting. The reactor temperature is preferably in the range of about 300° to about 650° C., more preferably about 500° to about 600° C. The weight hourly space velocity (WHSV) is not narrowly critical but will generally be within the range of about 0.1 to about 100 $hr^{-1}$, preferably from about 1 to about 20 $hr^-$. Any convenient pressure can be used, with the lowest practical pressure preferred in order to minimize side reactions such as polymerization. Preferred pressures are within the range of about 0.2 to about 500 psi more preferably about 7 to about 30 psi.

The isomerization feedstock contains at least one alkane and/or alkene, preferably alkanes having from 4 to about 12 carbon atoms per molecule, more preferably alkanes having from 4 to 6 carbon atoms per molecule. Alkenes or alkanes having 7 or more carbon atoms are generally more likely to crack into light gases than to undergo skeletal isomerization. The alkenes may have terminal or internal double bonds. Normal alkanes, especially normal butanes, are preferred feedstocks. Butene feedstocks may contain 1-butene, 2-butene or mixture thereof. Examples of other normal alkenes which are useful feedstocks are 1- and 2-pentenes; 1-, 2- and 3-hexenes; 1-, 2-, and 3-heptenes; and 1-, 2-, 3-, and 4-octenes. The normal alkenes can be accompanied by other hydrocarbons such as alkanes, typically other hydrocarbons having the same numbers of carbon atoms as the alkene feed. In the case of normal butenes, examples of other hydrocarbons are normal butane and isobutane.

Particular feedstocks contemplated for use in the present process are fractions containing n-butanes, optionally mixed with isobutane and n-butenes. Such fractions are commonly produced in petrochemical plants and refineries as, for example, after the separation of 1,3-butadiene from a $C_4$ cut or in the cracking of waxy distillates. Isobutene present in such fractions is commonly converted by catalytic reaction with methanol to produce methyl tertiary-butyl ether ("MTBE"). MTBE is separated by distillation, leaving a residual $C_4$ cut. Isobutene present in such fractions may also be oligomerized to produce oligomers which are then separated, again leaving a residual $C_4$ cut. In either MTBE production or oligomerization, a mixture of n-butenes, n-butane and isobutane remains in the residual material. It is desirable to produce additional isobutene from the residual material and return the isobutene for further conversion by the reactions mentioned above.

The isomerization feed stream can contain inert gaseous diluents (e.g. paraffins, $N_2$, steam, etc.). The diluent may be present in any desired proportion, e.g., up to about 80 weight percent of the feed stream. Hydrogen can be present in the feed stream in addition to such diluents, and with or without steam can have beneficial effects on the product yield and selectivity.

Selection of isomerization conditions is dependent on the alkanes and/or olefins to be isomerized. In general, lower temperatures are used for feeds containing larger olefin molecules. Depending on the specific skeletal isomerization catalysts chosen to carry out the steps of the invention, any suitable reaction technique can be utilized, such as fixed bed reaction, fluidized bed reaction, liquid phase batch and continuous operations, and the like. Conventional methods can be used to separate the materials present in the reaction effluent, including fractionation, crystallization, adsorption, and the like. Fractionation is generally preferred. Saturated materials which accumulate in the system can easily be removed by suitable techniques well known in the art.

In one aspect of the process according to the invention, the conversion of n-alkenes into isoalkenes, preferably n-butenes into isobutene, almost up to the establishment of thermodynamic equilibrium is achieved. This equilibrium, between 400° to 500° C., is about 36 to 40 percent by weight in the case in which the pure system of the n-butenes and isobutene is considered. This equilibrium is frequently not achieved in the case of a single contact of the mixture to be employed according to the invention with the catalyst to be employed during the invention. However, in a particular variant of the process, the product stream leaving the catalyst bed can be divided up, and only one part is directly conveyed to the working-up process, while the other part is again conducted over the catalyst bed. This division of the product stream for recycling can vary within wide limits, for example between the proportions 1:9 to 9:1 of worked-up or recycled material. In this process, a high recycling rate implies a smaller throughput, relative to a constant catalyst charge and constant remaining reaction conditions, but brings a desired shift of the spectrum of components in favor of the isoalkene, e.g. of the isobutene, almost to the thermodynamic equilibrium. On the other hand, a lower recycling rate implies a higher throughput but a poorer approach to the thermodynamic equilibrium. A decision concerning the amount of the recycling rate depends, other process parameters being constant, above all on the composition of the starting hydrocarbon mixture which is available. However, with the catalysts according to the invention, the process can, in general, be operated without a high recycling rate. This can be optimized by simple preliminary experiments.

Referring to FIG. 1, a preferred embodiment of the invention is directed to an integrated process for skeletal isomerization of normal butanes and/or butenes to produce isobutene, which is then used in the production of methyl tertiary-butyl ether (MTBE). Streams of a mixed butene feedstock (2) and methanol (4) are reacted in an MTBE synthesis reactor (6), the methanol reacting with the isobutene in the mixed feedstock to form MTBE which is taken off via line 8. The MTBE synthesis reactor acts as a $C_4$ separation unit, since the methanol reacts selectively with isobutene. Other mixed olefin streams could be treated in the same manner, e.g. reacting methanol with isoamylenes to form tertiary-amyl methyl ether (TAME). Other alcohol streams could be employed in a similar manner; e.g., reacting ethanol with mixed butenes to form ethyl tertiarybutyl ether (ETBE). The alcohol stream can contain at least one alkanol having from 1 to about 5 carbon atoms. Depending upon whether streams containing substantially single alcohols or mixtures thereof are employed, the corresponding alkyl tertiary-alkyl ether or mixtures containing various groups can be produced.

The product raffinate stream (10) is fed to the skeletal isomerization unit (12) wherein a catalyst of the present invention is employed to isomerize normal butenes and/or butanes to isobutene for recycle to the MTBE reactor via recycle line (14). Hydrogen (line 11) or steam (not shown) can be introduced into isomerization section (12) to improve reactor performance, as discussed infra. Saturated species which are unsuitable for isomerization can be separated and purged from the raffinate via line (15), or as part of the by-products ($C_1$–$C_3$ gases and polygas) which are separated from the isomerization section via lines (16) and (18). In addition to mixed butene feedstock entering the MTBE reactor (6) via line (2), feedstocks rich in alkanes can be introduced directly to the isomerization section 12 (line not shown) for one step isomerization to form isoolefins.

Such an integrated process permits a mixed feed stream of butenes (or other alkanes and/or alkenes) to be used most effectively in the production of MTBE (or other alkyl tertiary-alkyl ethers) via the skeletal isomerization of the normal alkanes and/or alkenes and recycle to the MTBE reactor. The skeletal isomerization processes and catalysts of the present invention are of course useful in processing feed streams containing normal alkanes and/or alkenes from a variety of sources, including, e.g., a dehydrogenation process.

Typically, prior art processes for the skeletal isomerization of olefins have required contacting the feedstock at elevated temperature with strongly acidic catalysts. Most of the metal oxide catalysts employed required treatment with halides to produce the required acidity, often requiring halide treatment during the reaction as well. Such halided catalysts involve significant corrosion problems as well as increased processing expenses. Furthermore, water and/or methanol must be rigorously excluded from the feeds contacting such catalysts, since their presence would deactivate the halided catalysts. In contrast, the catalysts of the present invention have been found to be impervious to poisoning by water in the feed and the addition of steam to the isomerization unit actually improves catalyst activity.

EXAMPLES

The invention is further illustrated by reference to the following non-limiting examples.

EXAMPLE 1

Synthesis of Boron-ZSM-11 Zeolites

A 25 gram quantity of Ludox AS40 (DuPont, 40% $SiO_2$) was added slowly with vigorously stirring to a mixture of solution which contained 2.07 g of $H_3BO_3$, 52.89 g of 55% tetra-n-butylammonium hydroxide (TBAOH) solution, and 189 ml of water. The addition of Ludox gave a curdy, gelatinous, milky slurry. The molar composition of the gel was:

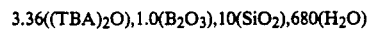

$$3.36((TBA)_2O), 1.0(B_2O_3), 10(SiO_2), 680(H_2O)$$

The solution had a pH of 13.0. The mixture was transferred to a Teflon liner and sealed in a steel autoclave. The autoclave was kept in an oven at 165° C. for 7 days. After that it was cooled and its contents were filtered. The recovered white crystalline material was washed with copious amounts of water and was dried at 110° C. for 16 h. The dried sample was calcined at 592° C. under nitrogen for 4 hours and then under air for another 2 hours to remove the organic template. The yield was 7.12 g and the sample contained 44.2% Si and 0.24% B. Thus, the approximate weight ratio of silicon to boron (Si/B) was 71.

Table 1, below, and FIG. 3 show the result of XRD analysis of the product. FIG. 2 shows the morphology of the sample in a scanning electron micrograph. These data indicate that a highly crystalline zeolite with the topology of the ZSM-11 zeolite and containing boron in the framework structure was obtained.

TABLE 1

| d Space Å | 100 I/Io |
|---|---|
| 11.20 | 44 |
| 10.07 | 37 |
| 7.45 | 4 |
| 7.10 | 2 |
| 6.70 | 3 |
| 6.36 | 2 |
| 6.06 | 7 |
| 6.00 | 6 |
| 5.58 | 4 |
| 5.01 | 3 |
| 4.61 | 5 |
| 4.36 | 9 |
| 3.845 | 100 |
| 3.718 | 36 |

TABLE 1-continued

| d Space Å | 100 I/Io |
|---|---|
| 3.653 | 8 |
| 3.479 | 3 |
| 3.393 | 2 |
| 3.348 | 3 |
| 3.059 | 5 |
| 2.984 | 9 |
| 2.957 | 2 |
| 2.612 | 2 |
| 2.502 | 2 |
| 2.489 | 3 |
| 2.399 | 2 |
| 2.005 | 8 |
| 1.923 | 2 |
| 1.875 | 2 |
| 1.868 | 2 |
| 1.674 | 2 |
| 1.665 | 2 |

Based upon these results, it is expected that [B]-ZSM-11 zeolites also can be synthesized under the following conditions:

1. The temperature of the hydrothermal synthesis can be between 80° to 220° C., the time ranging from 1 to 30 days. The preferable temperature and time are 165° C. and 7 days, respectively.
2. The pH of the mixture can be between 9 and 14, and the preferable pH is 13.
3. The silicon source can be colloidal silica, silica-gel, sodium silicate, and organic derivatives of silicon, such as tetraalkylsilicates.
4. The boron source can be boric acid, sodium borate, borax, and organic derivatives of boron, such as trialkylborates.
5. The organic template can be tetra-n-butylammonium hydroxide, tetra-n-butylammonium bromide, tetra-n-butylammonium chloride, or any suitable TBA salts.
6. The reaction mixture can be as indicated by the formula below,

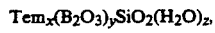

$$Tem_x(B_2O_3)_y SiO_2(H_2O)_z,$$

where for each mole of $SiO_2$, x is from 0 to 0.8, preferably 0.3 to 0.6; y is from greater than 0 to 0.5, preferably from greater than 0 to 0.1; and z is from 10 to 1000, preferably from 20 to 100.

7. If alkali salts were used in the synthesis, the zeolite will be in an alkali form. The zeolite has to be converted to a hydrogen form by ion-exchange with ammonium salts one or more times followed by drying and calcination.

8. The zeolite can be calcined under nitrogen, air, inert gases, or a combination of them. The temperature can be between 400° and 700° C. The preferable conditions are to calcine at 592° C. under nitrogen for 4 hours and then under air for 2 hours.

EXAMPLE 2

Preparation of Pt-Boron-ZSM-11 Catalysts

A 3 gram amount of the calcined sample from Example was mixed with 3.12 g of 20% alumina sol, 2 ml of 0.34 wt. % $Pt(NH_3)_4Cl_2.H_2O$ aqueous solution and 6.5 ml of water for few minutes. A 0.84 gram quantity of $NH_4OH$ was added dropwise to gel the mixture, followed by stirring until the gel had a pasty texture. The gel was then dried and calcined with air at 300° C. for 4 hours. The solid mass was crushed and sieved to between 28 to 35 meshes. The yield was 3.11 g. The catalyst contained 83 weight percent of [B]-ZSM-11, 17 weight percent of alumina binder, and 0.1 weight percent of Pt.

Using this example as a guideline, catalysts also can be prepared by the following methods:

1. The metal can be noble metals, metals selected from Groups IB, IIB, IIIB, IVB, VB, VIB, VIIB, VIII, and the rare earth elements, or combination thereof. The preferable metal is a noble metal such as platinum, palladium, or rhodium. Combination of such metals can be used.

2. The metal can be added by physical admixture, impregnation, immersion, ion-exchange techniques, or combinations thereof. Well-known standard procedures can be employed. If the ion-exchange technique is used, the zeolite can be in either a hydrogen form or an alkali form. If the impregnation technique is used, the zeolite should be in a hydrogen form.

3. Catalysts can be prepared with a binder such as alumina, silica, silica-alumina, clay or combinations of them, or without a binder.

4. The weight percent of metal can be between 0.01 to 30 wt. percent, and the weight percent of zeolite is between 0.1 to nearly 100 wt. percent. A representative composition of catalysts is approximately 0.1 wt. % metal, 83 wt. % zeolite, and 17 wt. % binder.

5. Suitable zeolites include [B]-ZSM-5 (Boralite C), [B]-ZSM-11 (Boralite-D), [B]-NU-1 (Boralite-A), [B]-Beta (Boralite-B), [B]-Mordenite and other borosilicates having pore sizes of at least about 5A.

EXAMPLE 3

Testing of Pt-Boron-ZSM-11 Catalysts

About 1 gram of catalyst prepared in Example 2 was loaded in a 0.5" ID stainless steel tube reactor. The sample was reduced by hydrogen (250 cc/min) at 493° C. for one hour, and then sulfided by hydrogen sulfide (1% $H_2S$ in hydrogen, 192 cc/min) at the same temperature for five minutes. A mixture of hydrogen (1.182 g/h), n-butane (11.88 g/h), and water (0.36 g/h) was then introduced into the reactor at 537° C. and 1 atm pressure. The WHSV was 13.5 hr.:, the ratio $H_2$/n-butane was 2.9, and steam was present as 3 volume percent of the mixture. During the reaction the product stream was analyzed by an on-line gas chromatograph (GC) system, employing a Varian Model 3400 instrument.

The results are shown below in Table 2.

TABLE 2

Catalyst: Pt-[B]-ZSM-11
Composition: B of [B]-ZSM-11, 0.24%; [B]-ZSM-11, 83%; Pt, 0.1%; $Al_2O_3$ binder, 17%.

| | Time on Stream (hours) | | | |
|---|---|---|---|---|
| | 1 | 2 | 3 | 4 |
| Conversion (carbon %) | 26 | 25 | 22 | 23 |
| Selectivity (carbon %) | | | | |
| Isobutylene | 21 | 23 | 23 | 23 |
| n-Butenes | 45 | 49 | 47 | 49 |
| i-Butane | 25 | 17 | 21 | 19 |
| $C_1$ to $C_3$ | 9 | 11 | 9 | 9 |
| $C_5+$ | 0 | 0 | 0 | 0 |
| Isobutylene to $C_4$ olefins ratio | 0.32 | 0.32 | 0.32 | 0.33 |
| Productivity of isobutylene (g/g-cat/h) | 0.55 | 0.54 | 0.47 | 0.52 |

EXAMPLES 4–10

Testing of Catalysts Under Varying Reaction Conditions Reaction Conditions

The catalyst of Example 3 was tested at different temperatures and hydrogen/n-butane ratios. The results are shown in Table 3.

TABLE 3

| | Examples | | | | | | |
|---|---|---|---|---|---|---|---|
| | 4 | 5 | 6 | 7 | 8 | 9 | 10 |
| Temp., C.° | 537 | 537 | 537 | 537 | 517 | 527 | 547 |
| n-Butane feeding rate, g/h | 11.4 | 11.9 | 12.35 | 12.8 | 12.35 | 12.35 | 12.35 |
| $H_2$ feeding rate, g/h | 1.8 | 1.2 | 0.8 | 0.35 | 0.35 | 0.35 | 0.35 |
| Steam feeding rate, g/h | 0.36 | 0.36 | 0.36 | 0.36 | 0.36 | 0.36 | 0.36 |
| WHSV, $hr^{-1}$ | 13.53 | 13.10 | 13.65 | 13.54 | 13.54 | 13.54 | 13.54 |
| $H_2$/n-butane | 4.54 | 2.88 | 1.92 | 0.78 | 0.78 | 0.78 | 0.78 |
| Conversion, carbon % | 15.25 | 23.49 | 21.65 | 25.41 | 19.96 | 21.77 | 26.77 |
| Selectivity, carbon % | | | | | | | |
| Isobutylene | 15 | 23 | 25 | 29 | 27 | 28 | 28 |
| n-Butenes | 46 | 48 | 50 | 48 | 49 | 51 | 47 |
| i-Butane | 28 | 19 | 15 | 8 | 11 | 8 | 8 |
| $C_1$ to $C_3$ | 11 | 10 | 10 | 12 | 10 | 8 | 13 |
| $C_5+$ | 0 | 0 | 0 | 3 | 3 | 5 | 4 |
| Isobutylene/total $C_4$ olefins | 0.25 | 0.32 | 0.34 | 0.37 | 0.36 | 0.35 | 0.37 |
| Productivity of isobutylene, g/g-cat/h | 0.24 | 0.51 | 0.56 | 0.75 | 0.49 | 0.57 | 0.74 |

Based upon these examples, it is expected that the process of structural isomerization of n-butane to produce isobutylene can also be carried out under the following conditions:

1. The reactor temperature can range between about 100° and 700° C., the pressure can range between about 2 to 500 psi the hydrogen/hydrocarbon ratio can range from 0 to about 10, and the space velocity (WHSV) can range from about 0.1 to 100 $hr^{-1}$. The most preferably reactor conditions are 567° C. 0.5 atm, hydrogen/hydrocarbon=0.8, and space velocity (WHSV)=13.

2. In addition to treating n-butane, the process also can be applied to other saturated and unsaturated light hydrocarbons such as n-pentane, i-butane, and butenes, to undergo reactions including dehydro-isomerization, dehydrogenation, and isomerization.

3. Water vapor can be between about 0.01 and about 20 volume percent of the total vapor contacting the catalyst. The most preferable water vapor content is about 3 volume percent.

4. The catalyst should be reduced first before it is employed in the reaction. Optionally, the catalyst can be sulfided as well before use in the reactor. The reduction and sulfidation temperatures can be between about 100° and 600° C. The most preferable temperature is about 490° C.

EXAMPLES 11 to 15

High Conversion Catalysts

Pt/[B]-zeolites are bifunctional catalysts for the conversion of n-butane to isobutylene. The first step is the dehydrogenation of n-butane to n-butenes on platinum. The second step is the isomerization of n-butenes to isobutylene on [B]-zeolites. It has been reported that in most hydroisomerization reactions, the isomerization reaction is the rate determining step, and the dehydrogenation reaction can reach an equilibrium easily by using 0.3 to 0.5 weight percent of platinum on the catalyst. Our results have shown that the dehydrogenation reaction is far below the equilibrium level when the catalysts contain only 0.1 percent Pt. However, as the platinum loading is increased above about 0.3 percent, platinum tends to sinter at high reaction temperatures, for example above about 560° C. Consequently, the isobutylene yield tends to decease with increased platinum loading.

The dehydrogenation of butanes is highly endothermic. Therefore, high temperatures, e.g. above about 550° C., are generally required to provide enough conversion for commercial applications. Table 4 below lists several commercial dehydrogenation processes and the high reaction temperatures required. Both Oleflex and STAR processes use platinum as a main component of the catalysts. To prevent the platinum from sintering, other metal components are used to form alloys with platinum, i.e. the so-called multimetallic catalysts. The Catofin process uses chromium oxide supported on alumina as the catalyst.

To improve the conversion at high temperatures, it is planned to employ multimetallic systems to prevent sintering of the platinum. Platinum-rhenium, a system used in reforming catalysts to enhance catalyst stability, was tested.

TABLE 4

Commercial Processes for Dehydrogenation of Isobutane

| Process | UOP Oleflex | Air Products Catofin | Phillips STAR | Snamprogetti-Yarsintez |
|---|---|---|---|---|
| Feed | i-C$_4$ | i-C$_4$ | i-C$_4$ | i-C$_4$ |
| Product | i-C$_4$= | i-C$_4$= | i-C$_4$= | i-C$_4$= |
| Conv. % | 50 | 60 | 54 | 50 |
| Sel. % | 92 | 84 | 93 | 91 |
| Yield % | 46 | 50 | 50 | 46 |
| Catalyst | Pt/Al$_2$O$_3$ | Cr$_2$O$_3$/Al$_2$O$_3$ | Pt/Sn/Zn/Al$_2$O$_3$ | Cr$_2$O$_3$/Al$_2$O$_3$ |
| Temp. °C. | 540–593 | 540–760 | 540–620 | 550–600 |

Several Pt,Re/[B]-ZSM-11 bimetallic catalysts with different loadings of Pt and Re were prepared and tested. Some results are shown below in Table 5. Examples 11, 12 and 13 used catalysts with metal loadings 0.3 weight percent Pt and 0.3 weight percent Re, similar to commercial reforming catalysts. Example 11 was tested for 8 hours, and exhibited high activity at the first hour: 39.4 percent conversion, 26.0 percent isobutylene selectivity, and 10.2 percent isobutylene yield. After 4 hours, the catalyst lost some of its activity. The averaged results over 8 hours were: 36.2 percent conversion, 26.1 percent selectivity, and 9.4 percent yield. Examples 12 and 13 were tested for 21 and 23 hours, respectively. Both runs produced slightly better conversions and yields than Example 11. The first 5 hours of Example 12 produced isobutylene yields higher than 11 percent. Sintering of platinum was apparently still a problem, as shown by the increase of n-butene selectivity and the decrease of isobutylene selectivity during the reaction. A regeneration procedure could be developed to improve the selectivity and yield of isobutylene over used catalysts.

TABLE 5

Testing of Pt,Re/[B]-ZSM-11 Catalysts

| | Example | | |
|---|---|---|---|
| | 11 | 12 | 13 |
| Catalysts | Pt,Re | | |

TABLE 5-continued

Testing of Pt,Re/[B]-ZSM-11 Catalysts

| | Example | | |
|---|---|---|---|
| | 11 | 12 | 13 |
| [B]-ZSM-11, 0.28% B, 0.3% Pt & 0.3% Re. | | | |
| Reaction Conditions: | 1 atm, 567° C., 3 Vol % steam, 12.5 WHSV, 0.8, H$_2$/n-butane. | | |
| Time of testing, hrs | 8 | 21 | 23 |
| Conversion, carbon % | 36.2 (39.4)[1] | 43.0 (41.7)[1] | 39.2 (39.9)[1] |
| Selectivity, carbon % | | | |
| Isobutylene | 26.1 (26.0) | 24.0 (26.4) | 25.3 (25.8) |
| n-Butenes | 53.2 (49.4) | 57.2 (49.6) | 55.0 (45.5) |
| i-Butane | 2.9 (3.5) | 2.8 (3.1) | 2.9 (3.7) |
| C$_1$ to C$_3$ | 16.1 (19.0) | 14.0 (17.4) | 13.9 (21.1) |
| C$_5$+ | 1.7 (2.2) | 2.0 (3.5) | 2.9 (3.9) |
| Yield of isobutylene, carbon % | 9.4 (10.2) | 10.3 (11.0) | 9.9 (10.3) |

[1] Averaged results are shown first, and the first hour results are shown in the parentheses.

Testing of Pt,Re-[B]-ZSM-5 Catalysts

Several Pt,Re-[B]-ZSM-5 bimetallic catalysts with different loadings of Pt and Re prepared and tested under the same reaction conditions as those of the Pt,Re-[B]-ZSM-11 catalysts. Some results are shown below in Table 6. Examples 14 and 15 used the same catalyst loaded with 0.3 weight percent Pt and 0.3 weight percent Re. Example 14 produced 25.3 percent conversion, 27.5 percent selectivity and 7.0 percent yield at the first hour; the averaged results over 11 hrs were 19.8 percent conversion, 29.1 percent selectivity and 5.7 percent yield. As shown by these examples, it was frequently observed that the catalyst had very high activity at the beginning, which quickly decreased during the first hour to reach a steady state. Since it takes about 35 minutes to finish an on-line G.C. analysis, to study the details of catalytic activity during the first hour would require off-line G.C. analyses. Example 15 produced 20.7 percent conversion, 28.0 percent selectivity and 5.8 percent yield at the first hour; the averaged results over 23 hrs were 19.8 percent conversion, 29.7 percent selectivity and 5.9 percent yield. These averaged results were quite reproducible. Compared to the Pt,Re-[B]-ZSM-11 catalysts, the Pt,Re-[B]-ZSM-5 catalyst produced much lower conversions and yields; however, the isobutylene selectivity was better. These catalysts functioned in a steady state, with no deactivation observed. It behaved more like a low metal loading catalyst.

TABLE 6

Testing of Pt,Re/[B]-ZSM-5 Catalysts

| | Example | |
|---|---|---|
| | 14 | 15 |
| Catalysts | Pt,Re [B]-ZSM-5, 0.40% B, 0.3% Pt & 0.3% Re. | |
| Reaction Conditions: | 1 atm, 567° C., 3 Vol % steam, 12.5 WHSV, 0.8, H$_2$/n-butane. | |
| Time of testing, hrs | 11 | 23 |
| Conversion, carbon % | 19.8 (25.3)[1] | 19.8 (20.7)[1] |
| Selectivity, carbon % | | |
| Isobutylene | 29.1 (27.5) | 29.7 (28.0) |
| n-Butenes | 52.7 (44.3) | 52.5 (50.4) |
| i-Butane | 0.0 (0.0) | 1.6 (1.8) |
| C$_1$ to C$_3$ | 15.8 (25.6) | 13.8 (16.3) |

TABLE 6-continued

| Testing of Pt,Re/[B]-ZSM-5 Catalysts | | |
|---|---|---|
| | Example | |
| | 14 | 15 |
| $C_{5}+$ | 2.4 (2.6) | 2.4 (3.5) |
| Yield of isobutylene, carbon % | 5.7 (7.0) | 5.9 (5.8) |

[1]Averaged results are shown first, and the first hour results are shown in the parentheses.

While the processes and catalysts of the invention have been particulary illustrated by examples of the skeletal isomerization of n-butane and n-butenes, they are equally applicable to similar isomaterizations of the high n-olefins such as n-pentenes, n-hexenes, n-heptenes and the like. Reasonable variations and modifications are possible within the scope of the disclosure without departing from the spirit or scope of the invention, which is defined solely by the appended claims.

We claim:

1. A process for producing branched chain olefins which comprises contacting a feedstock comprising at least one component selected from the group consisting of normal alkanes, normal alkenes and branched chain alkanes with a catalyst comprising a boron-substituted zeolite containing sufficient boron to provide sufficient acidity in said zeolite to dehydroisomerize both normal alkanes and alkenes and at least one noble metal, said zeolite being characterized by the topological structure of ZSM-11.

* * * * *